(12) United States Patent
Vargas et al.

(10) Patent No.: US 7,063,712 B2
(45) Date of Patent: *Jun. 20, 2006

(54) ANASTOMOSIS METHOD

(75) Inventors: Jaime Vargas, Palo Alto, CA (US); Michael Hendricksen, Menlo Park, CA (US); Stephen A. Yencho, Menlo Park, CA (US); Jamey Nielsen, San Francisco, CA (US); Bernard A. Hausen, Menlo Park, CA (US); Brendan Donohoe, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 677 days.

This patent is subject to a terminal disclaimer.

(21) Appl. No.: 10/253,347

(22) Filed: Sep. 24, 2002

(65) Prior Publication Data

US 2003/0028205 A1   Feb. 6, 2003

Related U.S. Application Data

(63) Continuation of application No. 09/842,792, filed on Apr. 27, 2001, now Pat. No. 6,478,804.

(51) Int. Cl.
  *A61B 17/04* (2006.01)
(52) U.S. Cl. ..................................... 606/153
(58) Field of Classification Search ............... 606/153; 227/175.1
See application file for complete search history.

(56) References Cited

U.S. PATENT DOCUMENTS

| | | | |
|---|---|---|---|
| 3,254,650 A | 6/1966 | Collito | |
| 3,254,651 A | 6/1966 | Collito | |
| 3,519,187 A | 7/1970 | Kapitanov et al. | |
| 3,774,615 A | 11/1973 | Lim et al. | |
| 4,214,587 A | 7/1980 | Sakura, Jr. | |
| 4,248,267 A | 2/1981 | Brandenberg | |

(Continued)

FOREIGN PATENT DOCUMENTS

DE   197 32 234 A   1/1999

(Continued)

OTHER PUBLICATIONS

Ethicon Endo-Surgery, "Atlas of Surgical Stapling" (1999).

*Primary Examiner*—Gary Jackson
(74) *Attorney, Agent, or Firm*—Brian A. Schar

(57) ABSTRACT

An anastomosis system and method uses an anvil to control and support a tissue site during an anastomosis procedure. The anvil is particularly useful for supporting a wall of a coronary artery during attachment of a graft vessel to the coronary artery because the wall of the coronary artery is very thin, difficult to grasp, and susceptible to tearing. In one method, the anvil is inserted into a pressurized or unpressurized target vessel and is pulled against an inner wall of the target vessel causing tenting of the thin tissue of the vessel wall. A graft vessel is then advanced to the anastomosis site and an end of the graft vessel is positioned adjacent and exterior of the target vessel. Staples are inserted through the tissue of the graft vessel and the target vessel by pivoting the arms of a staple holder towards the anvil. When the ends of the staples engage staple bending features on the anvil, the ends of the staples bend over securing the graft vessel and target vessel together. After stapling is complete, an incision is formed in the wall of the target vessel to allow blood flow between the target vessel and the graft vessel.

14 Claims, 9 Drawing Sheets

U.S. PATENT DOCUMENTS

| | | |
|---|---|---|
| 4,331,277 A | 5/1982 | Green |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,592 A | 6/1985 | Daniel |
| 4,553,542 A | 11/1985 | Schenck et al. |
| 4,593,693 A | 6/1986 | Schenck .................. 606/155 |
| 4,603,693 A | 8/1986 | Conta et al. |
| 4,605,001 A | 8/1986 | Rothfuss et al. |
| 4,607,637 A | 8/1986 | Berggren et al. |
| 4,617,928 A | 10/1986 | Alfranca |
| 4,624,255 A | 11/1986 | Schenck et al. |
| 4,624,257 A | 11/1986 | Berggren et al. |
| 4,657,019 A | 4/1987 | Walsh et al. |
| 4,665,906 A | 5/1987 | Jervis |
| 4,747,407 A | 5/1988 | Liu et al. |
| 4,752,024 A | 6/1988 | Green et al. |
| 4,773,420 A | 9/1988 | Green |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 4,938,408 A | 7/1990 | Bedi |
| 4,951,861 A | 8/1990 | Schulze et al. |
| 5,005,749 A | 4/1991 | Aranyi |
| 5,018,657 A | 5/1991 | Pedlick et al. |
| 5,062,842 A | 11/1991 | Tiffany |
| 5,104,025 A | 4/1992 | Main et al. |
| 5,119,983 A | 6/1992 | Green et al. |
| 5,156,310 A | 10/1992 | Biedenharn |
| 5,156,613 A | 10/1992 | Sawyer |
| 5,156,619 A | 10/1992 | Ehrenfeld |
| 5,172,845 A | 12/1992 | Tejeiro |
| 5,178,634 A | 1/1993 | Ramos Martinez |
| 5,193,731 A | 3/1993 | Aranyi |
| 5,205,459 A | 4/1993 | Brinkerhoff et al. |
| 5,211,683 A | 5/1993 | Maginot |
| 5,234,447 A | 8/1993 | Kaster et al. |
| 5,250,058 A | 10/1993 | Miller et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti |
| 5,300,065 A | 4/1994 | Anderson |
| 5,304,220 A | 4/1994 | Maginot |
| 5,314,435 A | 5/1994 | Green et al. |
| 5,314,468 A | 5/1994 | Ramos Martinez |
| 5,333,773 A | 8/1994 | Main et al. |
| 5,336,233 A | 8/1994 | Chen |
| 5,350,104 A | 9/1994 | Main et al. |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,417,361 A | 5/1995 | Williamson, IV |
| 5,431,322 A | 7/1995 | Green et al. |
| 5,443,497 A | 8/1995 | Venbrux |
| 5,447,514 A | 9/1995 | Gerry et al. |
| 5,452,836 A | 9/1995 | Huitema et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel |
| 5,465,896 A | 11/1995 | Allen et al. |
| 5,478,003 A | 12/1995 | Green et al. |
| 5,478,354 A | 12/1995 | Tovey et al. |
| 5,489,058 A | 2/1996 | Plyley et al. |
| 5,522,834 A | 6/1996 | Fonger et al. |
| 5,533,661 A | 7/1996 | Main et al. |
| 5,535,935 A | 7/1996 | Vidal et al. |
| 5,540,677 A | 7/1996 | Sinfosky |
| 5,558,667 A | 9/1996 | Yarborough et al. |
| 5,562,241 A | 10/1996 | Knodel et al. |
| 5,571,167 A | 11/1996 | Maginot |
| 5,580,067 A | 12/1996 | Hamblin et al. |
| 5,586,711 A | 12/1996 | Plyley et al. |
| 5,609,285 A | 3/1997 | Grant et al. |
| 5,611,794 A | 3/1997 | Sauer et al. |
| 5,632,432 A | 5/1997 | Schulze et al. |
| 5,632,433 A | 5/1997 | Grant et al. |
| 5,636,780 A | 6/1997 | Green |
| 5,643,340 A | 7/1997 | Nunokawa |
| 5,653,373 A | 8/1997 | Green et al. |
| 5,655,698 A | 8/1997 | Yoon |
| 5,657,921 A | 8/1997 | Young et al. |
| 5,662,258 A | 9/1997 | Knodel et al. |
| 5,669,544 A | 9/1997 | Schulze et al. |
| 5,669,918 A | 9/1997 | Balazs et al. |
| 5,669,934 A | 9/1997 | Sawyer |
| 5,676,670 A | 10/1997 | Kim |
| 5,695,504 A | 12/1997 | Gifford, III et al. |
| 5,702,412 A | 12/1997 | Popov et al. |
| 5,707,362 A | 1/1998 | Yoon |
| 5,707,369 A | 1/1998 | Vaitekunas et al. |
| 5,707,380 A | 1/1998 | Hinchcliffe et al. |
| 5,709,693 A | 1/1998 | Taylor |
| 5,711,472 A | 1/1998 | Bryan |
| 5,725,544 A | 3/1998 | Rygaard |
| 5,749,895 A | 5/1998 | Sawyer et al. |
| 5,776,130 A | 7/1998 | Buysse et al. |
| 5,797,920 A | 8/1998 | Kim |
| 5,799,857 A | 9/1998 | Robertson et al. |
| 5,816,471 A | 10/1998 | Plyley et al. |
| 5,817,113 A | 10/1998 | Gifford, III et al. |
| 5,824,015 A | 10/1998 | Sawyer |
| 5,827,265 A | 10/1998 | Glinsky et al. |
| 5,827,271 A | 10/1998 | Buysse et al. |
| 5,833,698 A | 11/1998 | Hinchliffe et al. |
| 5,865,730 A | 2/1999 | Fox et al. |
| 5,878,938 A | 3/1999 | Bittner et al. |
| 5,879,371 A | 3/1999 | Gardiner et al. |
| 5,904,697 A | 5/1999 | Gifford, III et al. |
| 5,915,616 A | 6/1999 | Viola et al. |
| 5,918,791 A | 7/1999 | Sorrentino et al. |
| 5,921,995 A | 7/1999 | Kleshinski |
| 5,944,730 A | 8/1999 | Nobles et al. |
| 5,976,159 A | 11/1999 | Bolduc |
| 5,993,464 A | 11/1999 | Knodel |
| 6,004,335 A | 12/1999 | Vaitekunas et al. |
| 6,015,416 A | 1/2000 | Stefanchik et al. |
| 6,024,748 A | 2/2000 | Manzo et al. |
| 6,036,700 A | 3/2000 | Stefanchik et al. |
| 6,039,733 A | 3/2000 | Buysse et al. |
| 6,050,472 A | 4/2000 | Shibata |
| 6,053,390 A | 4/2000 | Green et al. |
| 6,066,144 A | 5/2000 | Wolf et al. |
| 6,066,148 A | 5/2000 | Rygaard |
| 6,071,289 A | 6/2000 | Stefanchik |
| 6,083,234 A | 7/2000 | Nicholas et al. |
| 6,110,187 A | 8/2000 | Donlon |
| 6,117,148 A | 9/2000 | Ravo et al. |
| 6,176,413 B1 | 1/2001 | Heck et al. |
| 6,183,486 B1 | 2/2001 | Snow et al. |
| 6,187,019 B1 | 2/2001 | Stefanchik |
| 6,193,129 B1 | 2/2001 | Bittner |
| 6,193,734 B1 | 2/2001 | Bolduc et al. |
| 6,209,773 B1 | 4/2001 | Bolduc et al. |
| 6,248,117 B1 | 6/2001 | Blatter |
| 6,436,097 B1 | 8/2002 | Nardella |

| | | | |
|---|---|---|---|
| 6,514,263 B1 | 2/2003 | Stefanchik | |
| 6,520,973 B1 | 2/2003 | McGarry | |
| 6,530,932 B1 | 3/2003 | Swayze | |
| 6,623,494 B1 * | 9/2003 | Blatter ................ 606/153 | |

FOREIGN PATENT DOCUMENTS

| | | |
|---|---|---|
| EP | 1354559 A2 | 5/1995 |
| EP | 0 885 595 | 12/1998 |
| EP | 0 938 870 | 9/1999 |
| EP | 0 820 724 | 3/2000 |
| EP | 0 820 725 | 3/2000 |
| EP | 0 990 420 | 12/2000 |
| FR | 2 316 910 | 7/1996 |
| WO | 98/19625 | 5/1998 |
| WO | 99/11178 | 3/1999 |
| WO | 99/21491 | 5/1999 |
| WO | 00/12013 | 3/2000 |
| WO | 00/59380 | 10/2000 |

* cited by examiner

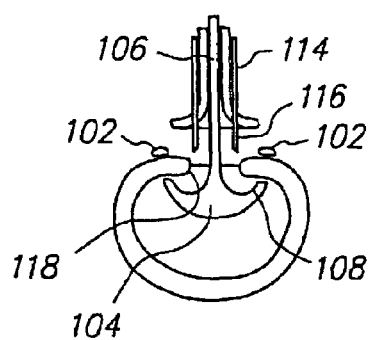 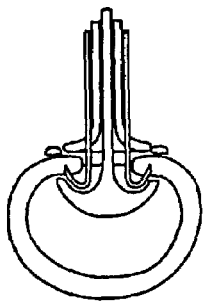 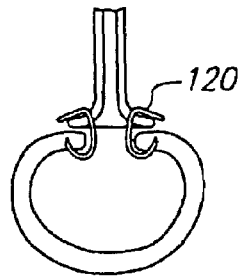
FIG. 20  FIG. 21  FIG. 22
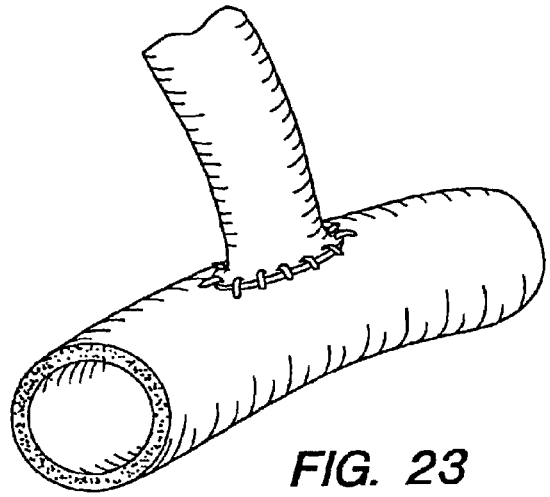
FIG. 23
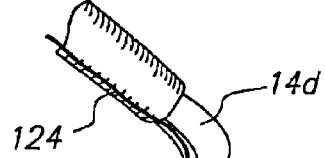
FIG. 24
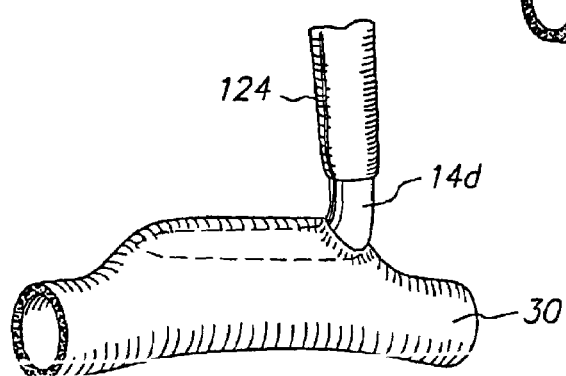
FIG. 25

ANASTOMOSIS METHOD

This application is a continuation of application Ser. No. 09/842,792, filed Apr. 27, 2001, now U.S. Pat. No. 6,478,804.

BACKGROUND OF THE INVENTION

1. Field of the Invention

The invention relates to an anastomosis system and method, and more particularly, the invention relates to an anastomosis system for controlling a tissue site during an anastomosis procedure.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery, such as the aorta. The suturing process is a time consuming and difficult procedure requiring a high level of surgical skill. In order to perform the suturing of the graft to a target vessel such as the coronary artery or the blood supplying artery the surgeon generally has an assistant hold the edges of the incision in the target vessel while the surgeon takes small stitches as close as possible to the edges of the incision. This suturing requires a high degree of precision and is quite time consuming. In addition, during conventional CABG procedures blood flow at the anastomosis site is stopped during suturing. This prevents bleeding from the incision site but also prevents blood from reaching a portion of the heart muscle served by the vessel.

Accordingly, it would be desirable to provide a vascular anastomosis system which allows the tissue at the anastomosis site to be controlled during suturing or other connection of the graft and target vessels. It would also be desirable to provide a vascular anastomosis system which allows the connection of a graft vessel to a target vessel prior to making an incision in the target vessel which allows blood flow between the target vessel and the graft vessel.

SUMMARY OF THE INVENTION

The present invention relates to an anastomosis system and method for controlling a blood vessel tissue site during an anastomosis procedure. The anastomosis system and method may be used on a pressurized vessel or on an unpressurized vessel. The anastomosis may be accomplished with sutures, staples, or other securing members.

In accordance with one aspect of the present invention, a method of controlling a tissue site during an anastomosis procedure includes the steps of inserting an anvil into a pressurized vessel at an intended anastomosis site, supporting a wall of the pressurized vessel at the intended anastomosis site with the anvil positioned adjacent an interior of the wall, performing anastomosis, and removing the anvil.

In accordance with another aspect of the invention, a method of controlling a tissue site during an anastomosis procedure includes the steps of inserting an anvil into a target vessel at an intended anastomosis site, supporting a wall of the target vessel at the intended anastomosis site with the anvil positioned adjacent an interior of the wall, performing anastomosis between a graft vessel and the target vessel, and making an incision in the wall of the target vessel to allow blood flow between the graft vessel and the target vessel.

In accordance with an additional aspect of the present invention, an anastomosis system for connecting a graft vessel to a target vessel includes an elongated anvil having substantially parallel staple bending features for bending the ends of staples, at least one staple with staple ends configured to be received by the staple bending features, and a staple holder for holding the at least one staple while puncturing tissue.

In accordance with a further aspect of the invention, an anvil for use in performing anastomosis between a graft vessel and a target vessel includes a handle, and an elongated anvil arm extending from the handle. The anvil arm has substantially parallel staple bending grooves or recesses for bending the ends of anastomosis staples. The elongated anvil arm is configured to be inserted into the target vessel beside an anastomosis site through a small incision which allows pressurization of the vessel to be maintained.

According to another aspect of the invention, a stapling system for use in performing anastomosis between a graft vessel and a target vessel includes a plurality of staples having ends configured to be inserted through tissue and bent over to secure the tissue, an expandable backbone supporting the plurality of staples for insertion. The backbone has an expandable configuration allowing a spacing between the plurality of staples to be changed.

In accordance with an additional aspect of the invention, a stapling system for use in performing anastomosis between a graft vessel and a target vessel includes a plurality of staples having ends configured to be inserted through tissue and bent over to secure the tissue, a staple strip holding the plurality of staples in a spaced arrangement for insertion into the tissue as a row of staples, and a frangible portion provided between each of the plurality of staples and the staple strip allowing the staples to be separated from the staple strip after insertion.

BRIEF DESCRIPTION OF THE DRAWINGS

The invention will now be described in greater detail with reference to the preferred embodiments illustrated in the accompanying drawings, in which like elements bear like reference numerals, and wherein:

FIGS. 20–22 are side cross sectional views of the steps of performing the anastomosis with the continuous anastomosis staple shown in FIG. 19;

FIG. 23 is a perspective view of the completed anastomosis performed as shown in FIGS. 19–22;

FIGS. 24–27 are perspective views of the steps of an alternative anvil and clamp system for controlling an anastomosis site and forming an incision through the clamped tissue of the target vessel;

DETAILED DESCRIPTION OF THE PREFERRED EMBODIMENTS

The anastomosis system and method according to the present invention uses an anvil to control and support a tissue site during an anastomosis procedure. The anvil is particularly useful for supporting a wall of a coronary artery during attachment of a graft vessel to the coronary artery because the wall of the coronary artery is very thin, difficult to grasp, and susceptible to tearing. Although the present invention is particularly useful for controlling very thin tissues such as the walls of the coronary arteries, the anvil may also be used for controlling other tissue sites.

Figure 1:
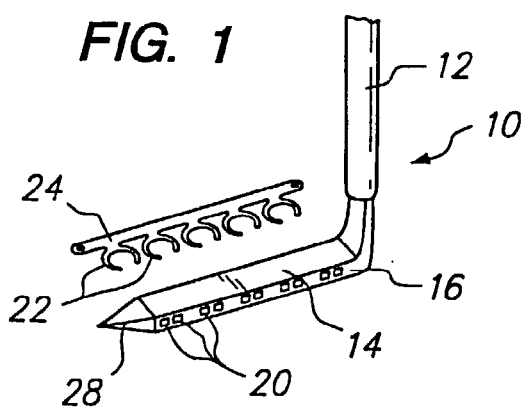
FIG. 1 is a perspective view of an anvil and a plurality of staples according to a first aspect of the present invention.

As shown in FIG. 1, an anvil 10 according to one aspect of the present invention includes a handle 12 and an anvil arm 14 extending substantially perpendicular from the handle. The anvil arm 14 is provided with several staple bending features 16 on opposite sides of the anvil arm 14. In the anvil shown in FIG. 1, the staple bending features 16 each include a plurality of recesses 20 which receive the ends of staples and cause the staple ends to bend over.

Also shown in FIG. 1 are a plurality of staples 22 connected to a staple holding strip 24. The staples 22 are preferably U-shaped staples which are arranged in a spaced apart parallel configuration such that the staples all lie in a single plane.

Figure 2:
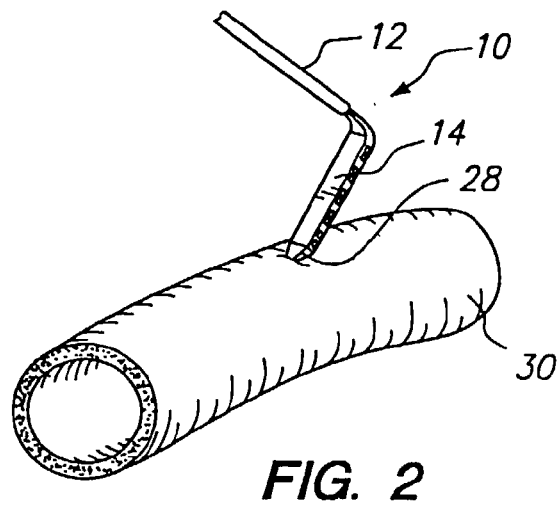
FIG. 2 is a perspective view of the anvil of FIG. 1 being inserted into a target vessel.

The anvil arm 14 has a sharp distal end 28 for puncturing the tissue of a target vessel to insert the anvil arm 14 into the target vessel. As illustrated in FIG. 2, the anvil arm 14 is inserted into a pressurized or unpressurized target vessel 30 by puncturing the target vessel with the distal end 28 of the anvil arm. The hole which is formed in the wall of the target vessel 30 by the anvil arm 14 is small enough to prevent significant bleeding through the puncture site. The hole is preferably less than 2 mm, and more preferably less than 1 mm in width.

Figure 3:
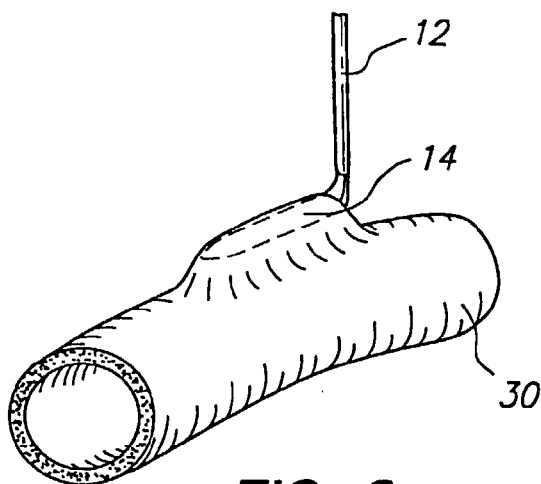
FIG. 3 is a perspective view of the anvil tenting a wall of a target vessel for an anastomosis procedure.

Once the anvil arm 14 has been inserted into the target vessel 30, the anvil arm 14 is pulled against an inner wall of the target vessel causing tenting of the thin tissue of the vessel wall as illustrated in FIG. 3. This tenting of the vessel wall provides control over the anastomosis site during an anastomosis procedure which is described with respect to FIGS. 4–6.

Figure 4:
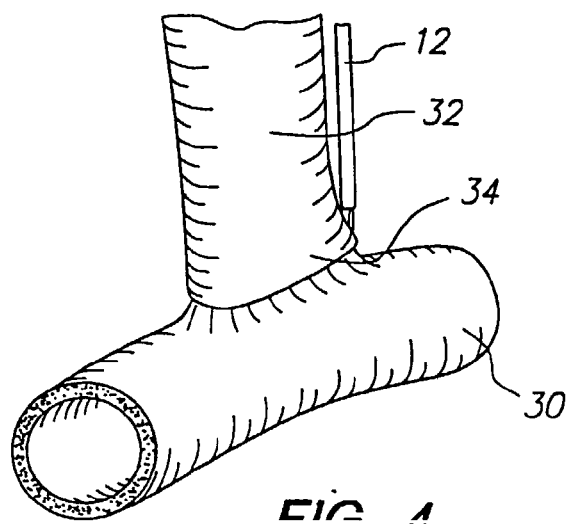
FIG. 4 is a perspective view of a graft vessel placed adjacent an exterior of the tented target vessel for the anastomosis procedure.
Figure 5:
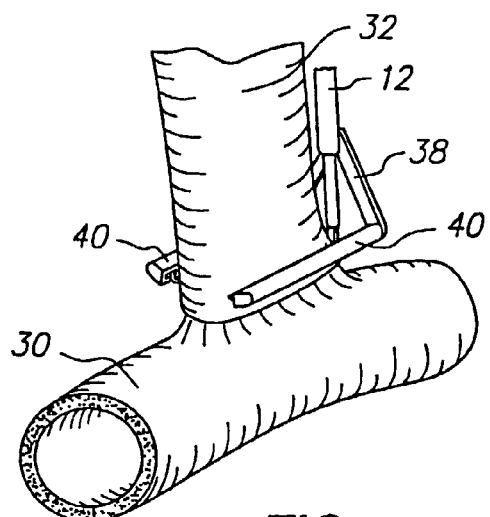
FIG. 5 is a perspective view of the staples being applied to the graft vessel and the target vessel during an anastomosis procedure.

As shown in FIG. 4, a graft vessel 32 is advanced to the anastomosis site and an end 34 of the graft vessel is positioned adjacent and exterior of the target vessel 30 at the anastomosis site. The tented portion of the target vessel 30 is inside the graft vessel in the step of FIG. 4. As shown in FIG. 5, a staple holder 38 is provided having two arms 40 which are pivotally connected to the handle 12 of the anvil. Alternatively, the pivoting arms 40 of the staple holder may be connected to a separate device. A staple holder 38 may be used to hold individual staples or preferably, the staple holder will hold the staple holding strips 24 as shown in FIG. 1. The staples 22 are inserted through the tissue of the graft vessel 32 and the target vessel 30 by pivoting the arms 40 of the staple holder 38 towards the anvil arm 14. When the ends of the staples 22 engage the staple bending features 16 on the anvil arm 14, the ends of the staples are bent over securing the graft vessel 32 and target vessel 30 together. Once the staple ends are bent over, the staples 22 are released from the staple holding strip 24 or the staple holder 38 resulting in spaced apart staples securing the graft vessel 32 and the target vessel 30 together as shown in FIG. 6.

After stapling is complete, an incision is formed in the wall of the target vessel 30 to allow blood flow between the target vessel and the graft vessel 32. Some examples of methods and devices for forming the incision will be described in further detail below. After completion of the anastomosis, the anvil arm 14 is withdrawn from the target vessel 30 between adjacent staples 22. The withdrawal of the anvil arm 14 leaves a gap which is approximately the same as the spacing between adjacent staples. Accordingly, no blood leakage occurs at the location where the anvil arm has been withdrawn.

Figure 6:
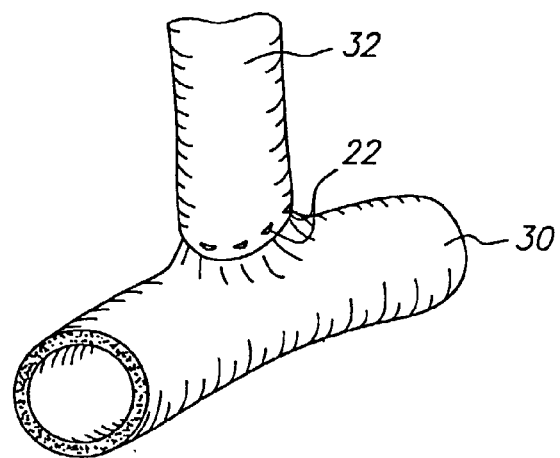
FIG. 6 is a perspective view of the completed anastomosis according to the first aspect of the present invention.

FIG. 6 illustrates a completed anastomosis between a target vessel 30 and a graft vessel 32 with a plurality of staples 22. A spacing between the staples 22 is preferably approximately 1 to 4 mm. This spacing is similar to the spacing between sutures in a conventional sutured anastomosis.

One example of an anvil arm 14 according to the present invention has a height and a width of about 2 mm or less, preferably about 1 mm or less, and a length of about 2 to 15 mm, preferably 5 to 12 mm. The length of the anvil will vary depending on the diameter of the graft vessel selected. Preferably, a length to width ratio of the anvil arm 14 is between 2:1 and 15:1.

The preferred staples 22 for use in the present invention have widths of about 0.2–3 mm, preferably about 2 mm or less and leg lengths of about 0.2–3 mm.

Figure 7:
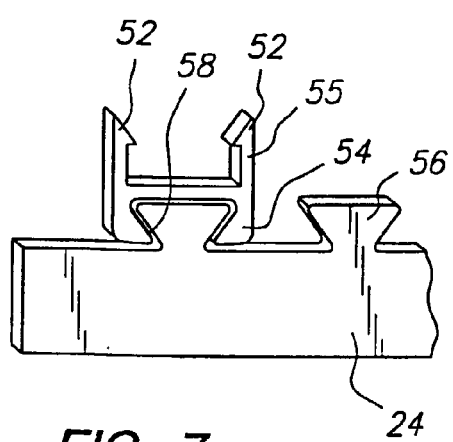
FIG. 7 is a perspective view of a staple supported on a staple holding strip.
Figure 8:
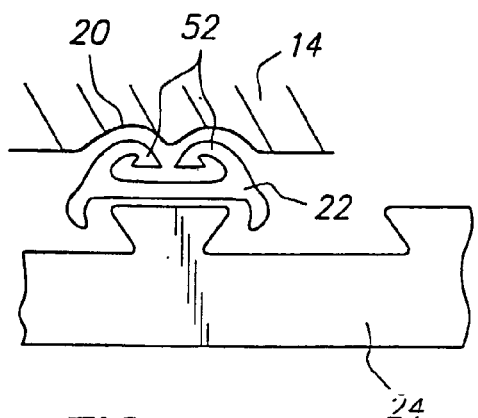
FIG. 8 is a side view of the staple and staple holding strip of FIG. 7 when the ends of the staple have been bent by contact with an anvil.

FIGS. 7 and 8 illustrate one example of a staple 22 connected to a staple holding strip 24. This staple 22 includes barbed staple ends 52 extending from the front portion of the staple and a C-shaped portion 54 extending from a rear of the staple for connecting the staple to the staple holding strip 24. The staple holding strip 24 includes a plurality of protrusions 56 for receiving the staples 22. The C-shaped portion 54 of the staple is received around one of the protrusions 56 and is preferably secured in place at one or more locations such as by welds 58 or other frangible portions. As shown in FIG. 8, when the staple holding strip 24 is advanced toward the anvil arm 14, the barbed staple ends 52 are received in the recesses 20 in the anvil arm causing the barbed staple ends to bend towards one another. At the same time that the barbed staple ends 52 bend over, or after the bending of the staple ends, the staple is detached from the staple holding strip 24. The staple 22 may be detached from the staple holding strip 24 by the action of bending the barbed staple ends, by bending a frangible connection between the staple holding strip and the staples to separate the staples, or any other known separation methods, such as melting of a connection between the staple and the staple holding strip.

Figure 9:
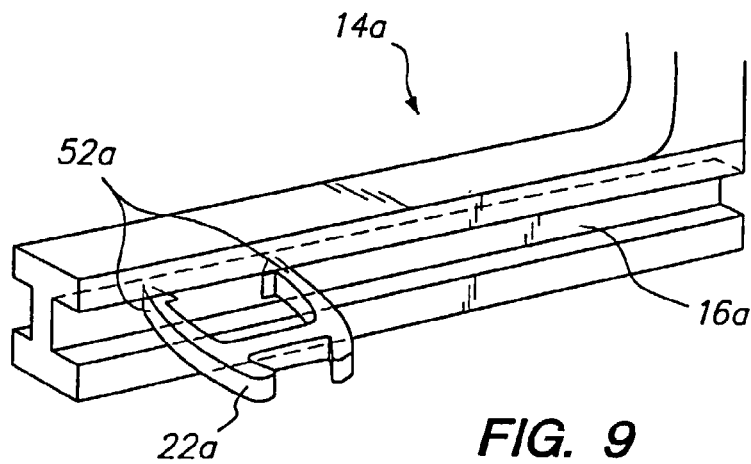
FIG. 9 is a perspective view of an anvil and staple according to another aspect of the present invention.

FIG. 9 illustrates an alternative embodiment of a staple 22a having inwardly curved barbed staple ends 52a. These inwardly curved barbed staple ends do not require the curved staple bending surfaces of the recesses 20 to bend the ends of the staples over. As shown in FIG. 9, the staple bending features 16a on the anvil arm 14a may be formed as a longitudinal groove along the anvil arm. When the curved ends 52a of the staple 22a are received in the groove 16a of the anvil arm 14a, the ends bend inward to secure the tissue with the staple.

Figure 10A:
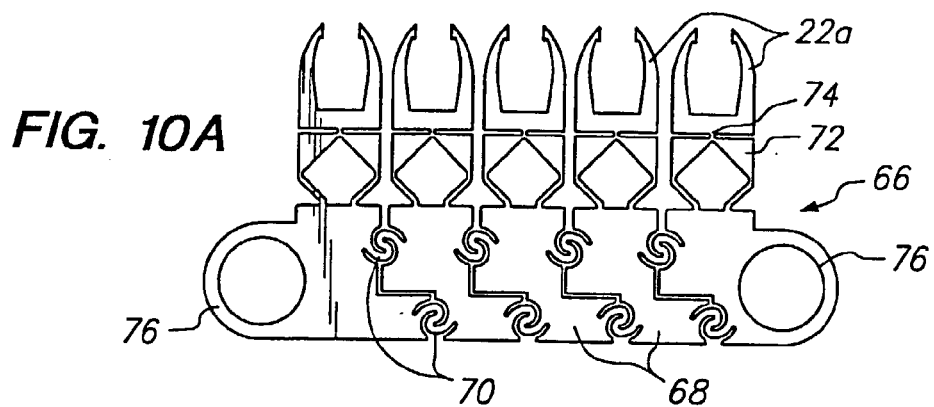
FIGS. 10A and 10B are is a side views of a plurality of staples supported on two embodiments of expandable staple holding strips.

FIG. 10A illustrates a plurality of staples 22a positioned on an expandable staple holding strip called an expandable backbone 66. The expandable backbone 66 includes a plurality of elements 68 which are interconnected by one or more expanding members 70. Each of the backbone elements 68 is provided with a connecting diamond member 72 which is connected to one of the staples 22a. According to the embodiment illustrated in FIG. 10A, the staples 22a are each connected to the diamond members 72 by a thin connecting section 74. The expandable backbone 66 allows the spacing between the staples 22a to be adjusted for the particular anastomosis to be performed. Preferably the backbone 66 allows expansion of the distance between staples from a distance of approximately 0.1 mm to a distance of approximately 1 to 4 mm, i.e., expansion of up to 40 times the original spacing.

The expanding backbone 66 also includes two openings 76 at opposite ends which may be engaged by pins on an anastomosis system or staple holder. The opening 76 allow the backbone to be easily expanded by relative motion of holding pins.

The connecting diamond members 72 are configured to collapse inwardly toward the backbone when the staples 22a engage the staple bending surfaces 16a of the anvil. The collapsing of the diamond members 72 forces the staples 22a to separate from the diamond members at the connecting sections 74.

Figure 10B:
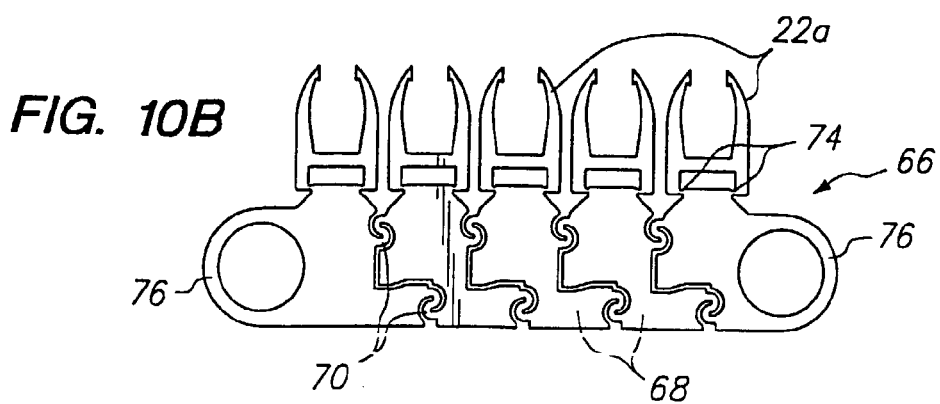

FIG. 10B illustrates an alternative embodiment of staples 22a and a backbone 66. In the embodiment of FIG. 10B, the staples 22a are each connected to the associated backbone elements 68 at two connecting sections 74.

Figure 11:
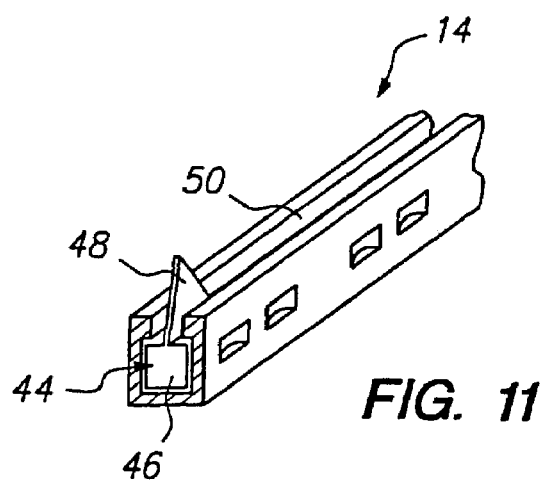
FIG. 11 is a perspective view of a portion of an anvil having a movable cutting device.

FIG. 11 shows a portion of an anvil arm 14 with a movable cutting device 44. The cutting device 44 includes a base 46 and a blade 48. The base 46 of the cutting device 44 is positioned in a longitudinal groove 50 in the anvil arm 14. After the anvil arm 14 has been inserted into the target vessel, the cutting device 44 may be moved longitudinally along the anvil arm to form an incision in the target vessel.

Figure 12:
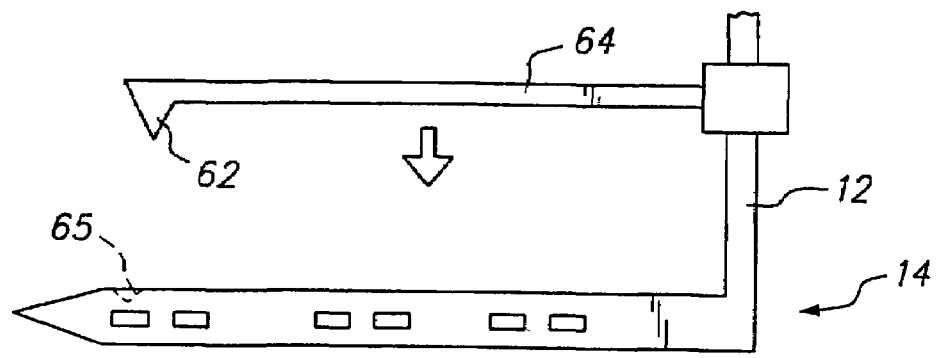
FIG. 12 is a side view of an anvil having an external cutting device.
Figure 12A:
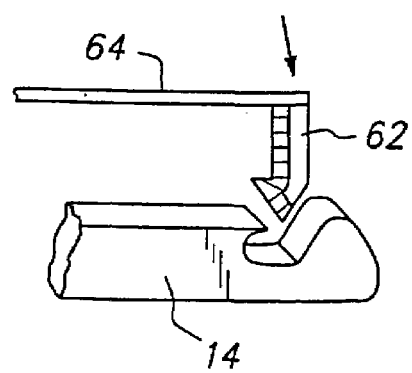
FIGS. 12A and 12B are side views of a portion of an anvil and two cutting devices which snap onto the anvil.
Figure 12B:
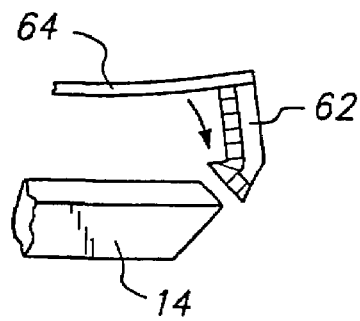

FIGS. 12, 12A, and 12B illustrate external cutting devices which are advanced down onto the anvil 14 after the anastomosis procedure and cut an incision in the target vessel from an exterior of the target vessel as the anvil is withdrawn. As shown in FIG. 12, a knife 62 is positioned on a knife arm which is movable along the handle 12 of the anvil. The knife 62 is moved downward until the knife engages a recess 65 in the anvil 14. As the anvil 14 is withdrawn from the anastomosis site, the knife 62 forms the incision in the target vessel.

FIGS. 12A and 12B illustrate two alternative embodiments of the knife 62 which snap onto a corresponding engagement surface 65 of the anvil 14 so that the knife and anvil are secured together for formation of the incision during removal of the anvil from the anastomosis site.

Figure 13:
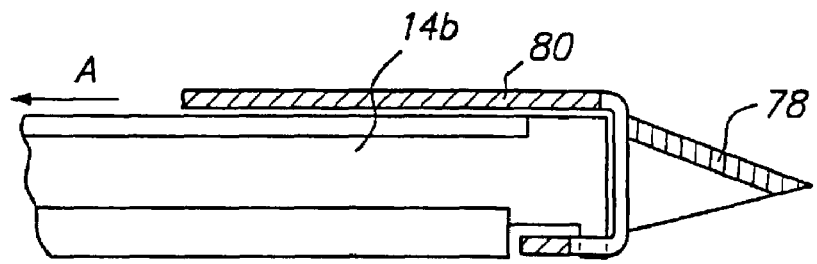
FIG. 13 is a side view of a portion of an anvil with an extendable cutting device.
Figure 14:
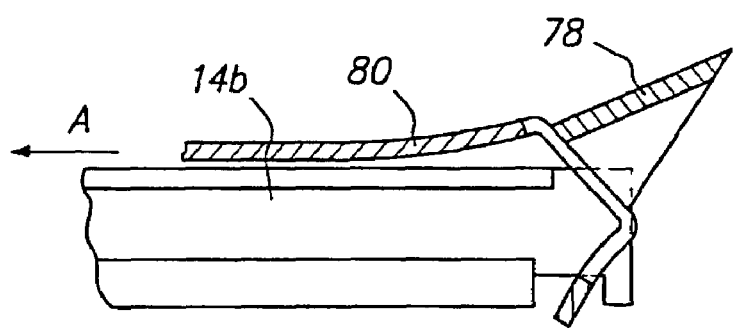
FIG. 14 is a side view of the anvil of FIG. 13 with the cutting device extended.

FIGS. 13–16 illustrate two variations of extendable cutting devices for making an incision in the target vessel while drawing the anvil arm 14 from the target vessel. FIG. 13 illustrates an anvil arm 14b having a blade 78 connected to a blade support 80. When the blade support 80 is pulled in the direction of the arrow A with respect to the anvil arm 14b, the blade 78 moves from a forwardly extending position shown in FIG. 13 to an upwardly extending position shown in FIG. 14. The blade 78 in the forwardly extending position may be used to form the small opening to insert the anvil arm 14 into the target vessel. After an anastomosis has been performed, the blade 78 is moved to an upwardly angled or a vertical position in which the blade is used to form an incision in the target vessel as the anvil arm 14b is removed from the target vessel.

Figure 15:
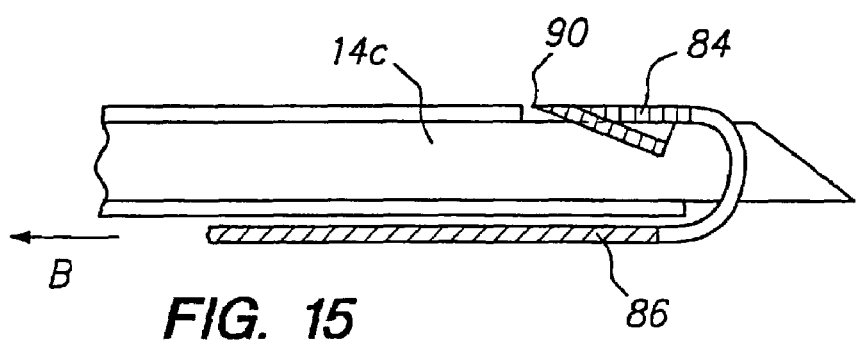
FIG. 15 is a side view of a portion of an anvil with an alternative embodiment of an extendable cutting device.
Figure 16:
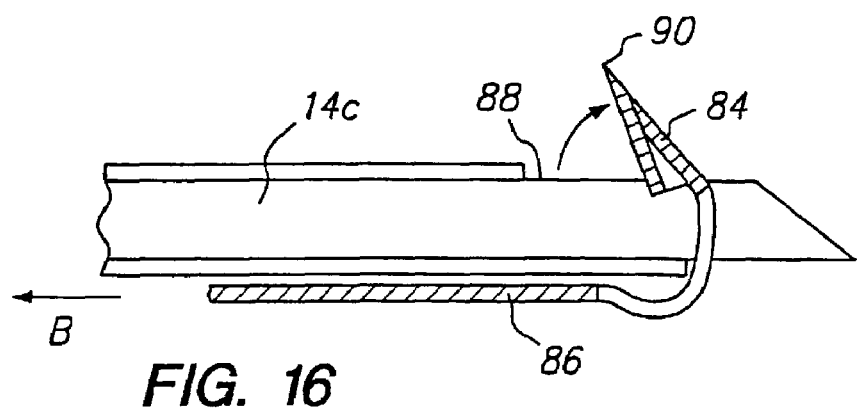
FIG. 16 is a side view of the anvil of FIG. 15 with the cutting device extended.

FIGS. 15 and 16 illustrate an alternative embodiment of an anvil arm 14c having a blade 84 and a blade support 86.

While the anvil arm 14c is being inserted into the target vessel and during the anastomosis procedure, the blade 84 is positioned in a recess 88 in the anvil arm. The blade 84 may be moved from the position of FIG. 15 to the extended position of FIG. 16 by moving the blade support 86 in the direction of the arrow B with respect to the anvil arm. Alternatively, the blade 84 may be extended automatically upon withdrawal of the anvil arm 14 when a blade tip 90 catches on an interior surface of the target vessel wall during withdrawal of the anvil arm.

The examples of extendable cutting devices for use with the anvil according to the present invention which are shown in FIGS. 13–16, are merely shown as examples of the type of cutting devices which may be used for making the incision. Once these cutting devices or blades have been extended from the anvil arm, they may be fixed to perform cutting as the anvil arm is removed from the target vessel or the blades may be movable along the anvil arm to make an incision prior to removal of the anvil arm from the target vessel.

Figure 17:
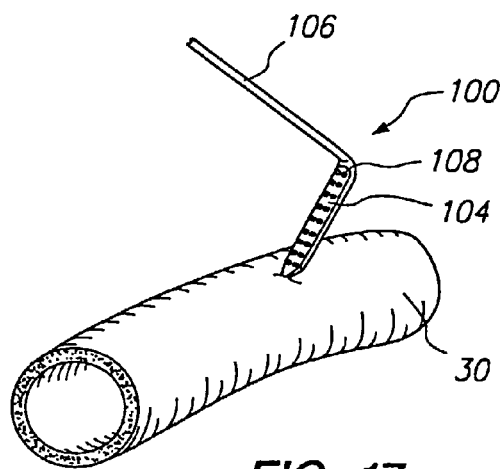
FIG. 17 is a perspective view of an anvil according to a second aspect of the invention being inserted into a target vessel.
Figure 18:
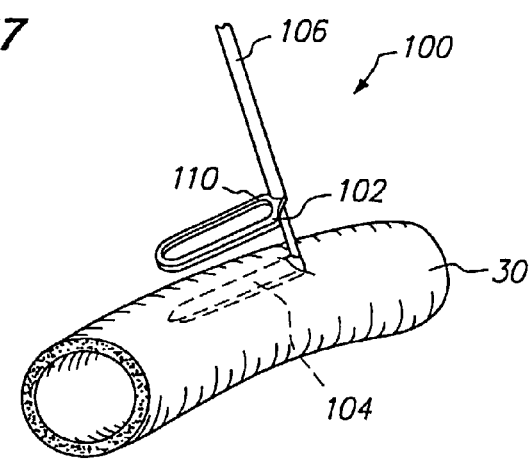
FIG. 18 is a perspective view of the anvil of FIG. 17 positioning inside a target vessel and a clamp being advanced to clamp the wall of the target vessel between the anvil and the clamp.

FIGS. 17–23 illustrate an alternative embodiment of an anvil 100 which is used with a clamp 102 for controlling an incision site during an anastomosis procedure. As shown in FIGS. 17 and 18, the anvil 100 includes an anvil arm 104 and a handle 106. The clamp 102 is slidable on the handle 106 to clamp the tissue of the target vessel 30 between the clamp 102 and the anvil arm 104. As in the embodiments discussed previously, the anvil arm 104 includes two rows of staple bending features 108 in the form of recesses positioned in two parallel rows along a top surface of the anvil. The clamp 102 has a central opening 110. Once the tissue of the target vessel wall has been trapped between the clamp 102 and the anvil arm 104, an incision may be made through the target vessel wall and the edges of the incision are controlled by the combination of the anvil and the clamp.

Figure 19:
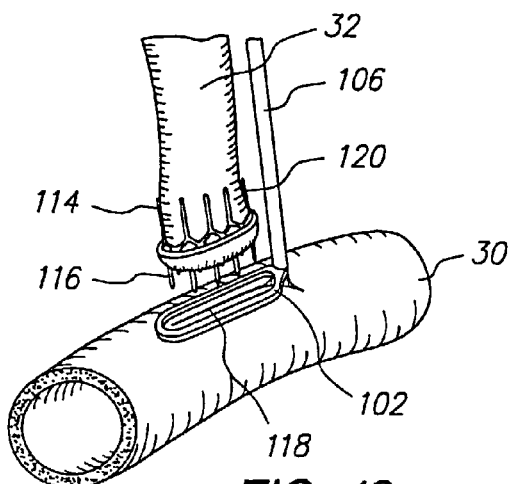
FIG. 19 is a perspective view of a graft vessel being advanced to the target vessel with a continuous anastomosis staple while the anastomosis site on the target vessel is controlled by the anvil and clamp.

As shown in FIG. 19, a continuous anastomosis staple device 114 may be used to connect the graft vessel 32 to the target vessel 30 at the anastomosis site. The staple device 114 as shown in FIG. 19 includes a plurality of linkages forming a tubular configuration and a plurality of staple ends extending from the linkages. FIGS. 20–22 illustrate how the staple ends 116 of the staple device 114 are positioned in the end of the graft vessel 32 and are inserted through the incision 118 in the target vessel and bent over by contact with the staple bending features 108 of the anvil. As shown in FIG. 22, the opposite ends 120 of the staple device 114 are folded over to complete the anastomosis. FIG. 23 illustrates a completed anastomosis performed according to the steps illustrated in FIGS. 19–22.

Figure 26:
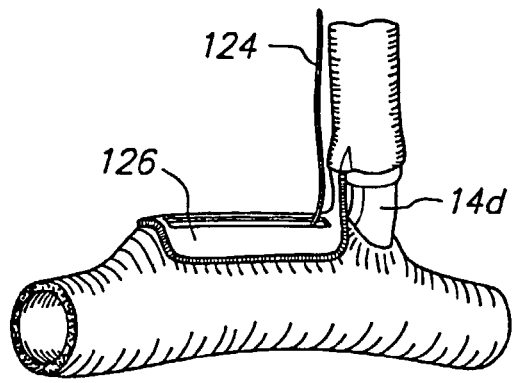
Figure 27:
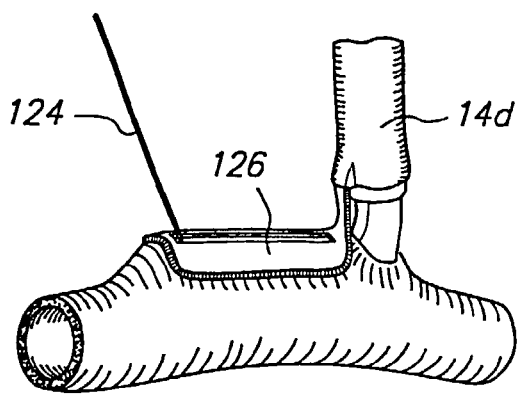

FIGS. 24–27 illustrate an alternative embodiment of an anvil having a 14d cutting wire 124 for forming the incision in the wall of the target vessel 30. The cutting wire 124 of FIGS. 24–27 may be used to form an incision either before or after performing an anastomosis procedure. For forming the incision after the anastomosis procedure, a clamp 126 is used to trap the tissue at the anastomosis site between the clamp and the anvil prior to performing the incision as shown in FIGS. 26 and 27.

Figure 28:
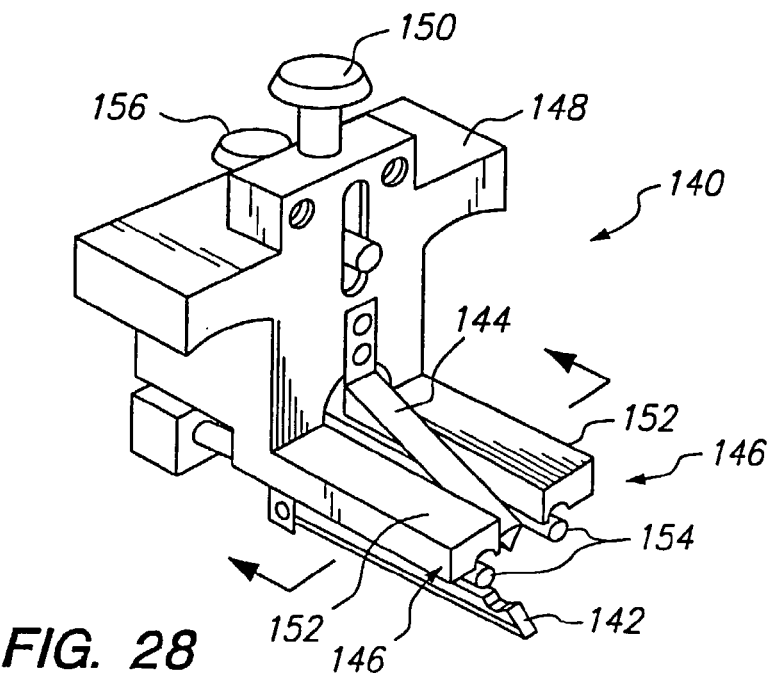
FIG. 28 is a perspective view of a system for controlling a tissue site and performing anastomosis according to the present invention.

FIG. 28 shows a system 140 for controlling a tissue site and performing anastomosis according to the present invention. For purposes of clarity, the staple holder and staples have been omitted from FIG. 28. The system 140 includes an anvil 142, a cutter 144, and a graft vessel holder 146 all mounted on a handle 148. The anvil 142 is mounted on the handle 148 and connected to an actuator 150 which allows the anvil to be moved downward against the bias of a spring inside the handle. The cutter 144 may be spring biased or fixed and is positioned on the handle 148 directly above the anvil 142. The graft vessel holder 146 includes two fixed arms 152 and two movable arms 154. The two movable arms 154 are connected to a second actuator 156 on the handle 148. Depression of the second actuator 156 against the bias of a spring within the handle causes the movable arms 154 to be moved downward away from the fixed arms to receive portions of a graft vessel between the movable and fixed arms.

Figure 29:
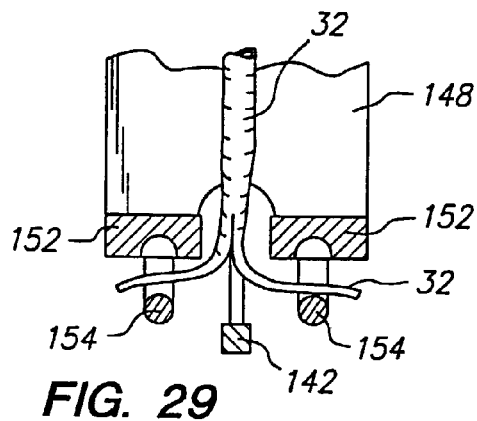
FIG. 29 is a cross sectional view taken along line C—C of FIG. 28, showing a first step of the anastomosis procedure.
Figure 30:
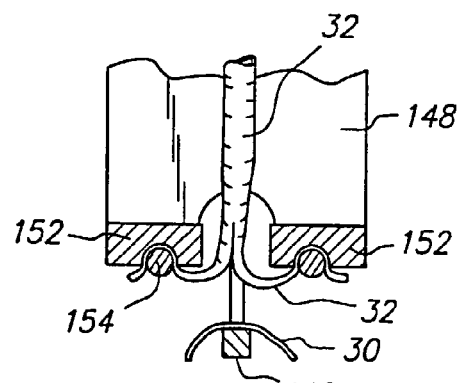
FIG. 30 is a cross sectional view taken along line C—C of FIG. 28, showing a second step of the anastomosis procedure.
Figure 31:
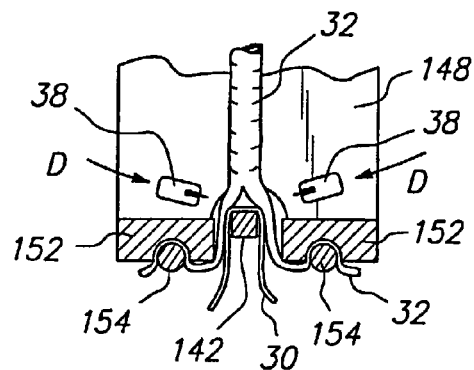
FIG. 31 is a cross sectional view taken along line C—C of FIG. 28, showing a third step of the anastomosis procedure.

The operation of the system 140 of FIG. 28 is shown in the cross sectional views of FIGS. 29–31. As shown in FIG. 29, an end of a graft vessel 32 is split so that the two halves of the graft vessel can be held by the graft vessel holder 146. In order to load the graft vessel into the system 140, the first actuator 150 and the second actuator 156 are depressed to move the anvil 142 and the movable arms 154 downward. The split graft vessel 32 is then inserted between the fixed and movable arms 152, 154 and the second actuator 156 is released to trap the ends of the graft vessel, as shown in FIG. 30. The anvil 142 is then inserted into the target vessel 30 as described above with respect to the various other anvil embodiments.

Once the anvil has been inserted in the target vessel 30 as shown in FIG. 30, the actuator 150 is released to allow the anvil to move upward to tent the wall of the target vessel. FIG. 31 illustrates the tented target vessel 30 positioned adjacent the split and trapped graft vessel 32 in a position for performing anastomosis. The staple holders 38 are then advanced in the direction of the arrows D toward opposite sides of the anvil to staple the graft vessel and target vessel together. Preferably, the staple holders hold a staple strip with an expandable backbone as shown in FIGS. 10A and 10B. The holders 38 may be provided with movable pins which allow a spacing between the staples to be adjusted depending on a size of the graft vessel used. Once the staples have been placed the anvil 142 is removed and the cutter 144 makes an incision in the target vessel during removal of the anvil.

Figure 32:
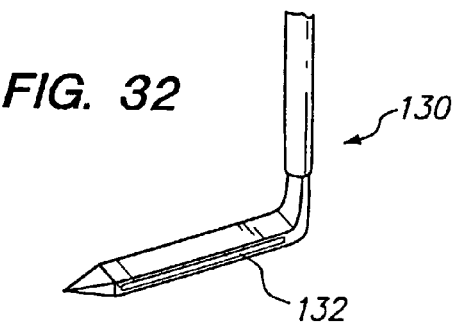
FIG. 32 is a perspective view of an anvil according to another aspect of the present invention for use with sutures.
Figure 33:
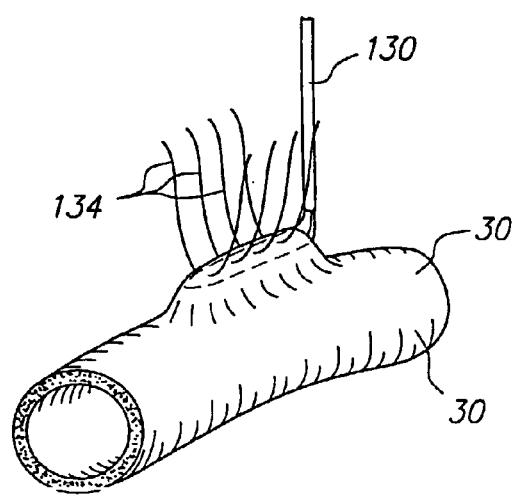
FIG. 33 is a perspective view of the anvil of FIG. 32 positioned within a target vessel and used to locate a plurality of suture at an anastomosis site.

FIGS. 32 and 33 illustrate the use of an anvil 130 for controlling the tissue at an anastomosis site. The anvil 130 includes a longitudinal slot 132 extending through the anvil for application of a plurality of conventional sutures at the anastomosis site. According to this method, the anvil 130 is inserted into the target vessel 30 and pulled against the interior wall of the target vessel, tenting the target vessel as shown in FIG. 33. Sutures 134 are then passed through the slot 132 in the anvil 130 and through the tissue of the target vessel wall on opposite sides of the anvil. Once the sutures are placed as shown in FIG. 33, an incision is made in the target vessel along a center of the anvil 130. A center portion of each of the sutures 34 is then pulled out through the incision in the target vessel and cut so that an even row of sutures is provided along each of the sides of the incision. This system eliminates the tedious procedure of placing each individual suture very close to the edge of the incision in the very thin and flexible target vessel wall. Each of the sutures 134 are connected to a graft vessel in a conventional manner completing the anastomosis. The anvil as shown in FIGS. 32 and 33 allows quick and easy placement of a plurality of sutures in a very even manner close to the edge of the incision. For example, the sutures of a conventional anastomosis are generally within about one millimeter of the edge of the incision and are preferably within 0.5 millimeters of the edge of the incision.

The invention has been described as including staple bending features provided on the anvil and staples provided at an exterior of the tissue. According to an alternative embodiment of the invention, the staples and/or staple holding strips may be positioned on the anvil and an exterior member with staple bending features may be moved toward the anvil to bend the ends of the staples and secure the graft and target vessels together.

While the invention has been described in detail with reference to the preferred embodiments thereof, it will be apparent to one skilled in the art that various changes and modifications can be made and equivalents employed, without departing from the present invention.

What is claimed is:

1. A method of performing anastomosis between a graft vessel and a target vessel, comprising:
    inserting an anvil into the target vessel through an anvil entrance hole, wherein upon insertion said anvil is positioned at least partially within the lumen of the target vessel;
    supporting the wall of the target vessel with said anvil;
    securing the graft vessel to the target vessel with a plurality of discrete connectors, said securing performed at a location on the target vessel spaced apart from the anvil entrance hole a distance not substantially greater than the length of said anvil; and
    removing said anvil from the anvil entrance hole.

2. The method of claim 1, wherein said connectors are staples.

3. The method of claim 1, further comprising creating an opening in the wall of the target vessel to allow fluid flow between the graft vessel and the target vessel.

4. The method of claim 3, further comprising a cutter moveable relative to said anvil, wherein said creating is performed by moving said cutter.

5. The method of claim 3, wherein the anvil entrance hole is spaced apart from the opening.

6. The method of claim 1, wherein substantially no leakage occurs through the anvil entrance hole after said removing.

7. The method of claim 1, wherein said creating is performed from inside the target vessel.

8. A method of performing anastomosis between a graft vessel and a target vessel, comprising:
    placing an end of the graft vessel against the side of the target vessel at a first location;
    inserting an anvil through the side of the target vessel at a second location adjacent to said first location;
    deploying a plurality of connectors to secure the graft vessel to the target vessel; and
    creating an opening in the target vessel to allow fluid flow between the graft vessel and the target vessel.

9. The method of claim 8, wherein said inserting comprises pressing said anvil through the side of the target vessel.

10. The method of claim 8, wherein said second location is upstream from said first location.

11. The method of claim 8, wherein said connectors are staples.

12. The method of claim 8, wherein said deploying includes bringing at least one said connector into contact with said anvil.

13. The method of claim 8, further comprising a cutter moveable relative to said anvil, wherein said creating comprises incising the target vessel with said cutter.

14. The method of claim 8, wherein said creating is performed from inside the target vessel.

* * * * *